US008772359B2

(12) United States Patent
Swazey

(10) Patent No.: US 8,772,359 B2
(45) Date of Patent: *Jul. 8, 2014

(54) SURFACTANT THICKENED SYSTEMS COMPRISING MICROFIBROUS CELLULOSE AND METHODS OF MAKING SAME

(75) Inventor: John M. Swazey, San Diego, CA (US)

(73) Assignee: CP Kelco U.S., Inc., Atlanta, GA (US)

( * ) Notice: Subject to any disclaimer, the term of this patent is extended or adjusted under 35 U.S.C. 154(b) by 851 days.

This patent is subject to a terminal disclaimer.

(21) Appl. No.: 11/611,492

(22) Filed: Dec. 15, 2006

(65) Prior Publication Data

US 2008/0108541 A1 May 8, 2008

Related U.S. Application Data

(63) Continuation-in-part of application No. 11/557,622, filed on Nov. 8, 2006.

(51) Int. Cl.

*B01F 3/12* (2006.01)
*B01F 17/00* (2006.01)
*B01F 17/48* (2006.01)
*C11D 3/22* (2006.01)
*C11D 17/00* (2006.01)
*A61K 9/10* (2006.01)
*A61K 8/04* (2006.01)
*A61Q 19/00* (2006.01)

(52) U.S. Cl.

CPC . *C11D 3/222* (2013.01); *B01F 3/12* (2013.01); *C11D 17/0004* (2013.01); *Y10S 516/903* (2013.01)

USPC ............... 516/31; 516/77; 516/106; 516/903; 510/416; 510/418; 510/535; 106/162.8

(58) Field of Classification Search

CPC ........ B01F 3/12; C11D 3/222; C11D 17/0004

USPC ............. 516/31, 77, 106, 903; 510/416, 418, 510/535; 106/162.8

See application file for complete search history.

(56) References Cited

U.S. PATENT DOCUMENTS 3,858,854 A 1/1975 Win et al.
4,378,381 A * 3/1983 Turbak et al. ................. 426/570
4,379,059 A 4/1983 Hockey et al.
4,452,722 A * 6/1984 Turbak et al. ................. 516/106
4,483,743 A * 11/1984 Turbak et al. ................. 162/100
4,500,546 A * 2/1985 Turbak et al. ................. 514/781
5,087,471 A * 2/1992 Combes et al. ............... 426/573
5,441,753 A * 8/1995 McGinley et al. .............. 426/96
5,951,910 A 9/1999 Skaggs et al.
5,998,349 A 12/1999 Guillou
6,224,663 B1 * 5/2001 Cantiani et al. ............ 106/162.8
6,231,651 B1 5/2001 Schultz et al.
6,241,812 B1 * 6/2001 Smith et al. ................ 106/162.8
6,302,209 B1 10/2001 Thompson et al.
6,306,207 B2 10/2001 Cantiani et al.
6,846,785 B2 1/2005 Patel et al.
6,967,027 B1 * 11/2005 Heux et al. ..................... 424/488
7,888,308 B2 * 2/2011 Swazey ......................... 510/470
7,981,855 B1 * 7/2011 Palla-Venkata et al. ...... 510/462
7,994,111 B2 * 8/2011 Caggioni et al. .............. 510/473
8,097,574 B2 * 1/2012 Heath et al. ................... 510/137
8,361,239 B2 * 1/2013 Bettiol et al. ................ 134/25.2
8,470,755 B1 * 6/2013 Tajmamet et al. ............ 510/237
8,541,355 B2 * 9/2013 Fleckenstein et al. ........ 510/405
8,546,318 B2 * 10/2013 D'Ambrogio et al. ........ 510/470
2003/0109391 A1 6/2003 Midha et al.
2003/0162689 A1 8/2003 Schymitzek
2004/0267006 A1 12/2004 Yamane et al.
2005/0119151 A1 6/2005 Mayer et al.
2006/0029625 A1 2/2006 Niebauer
2006/0083761 A1 4/2006 Yoshimi et al.
2006/0110416 A1 * 5/2006 Ryles et al. ................... 424/401
2006/0127345 A1 6/2006 Hilvert et al.
2006/0281859 A1 12/2006 Suzuki et al.
2007/0027108 A1 2/2007 Yang et al.
2007/0197779 A1 8/2007 Yang et al.
2008/0108541 A1 * 5/2008 Swazey ......................... 510/535
2008/0108714 A1 * 5/2008 Swazey et al. .................. 516/31
2010/0009891 A1 * 1/2010 Canto et al. ................... 510/418
2010/0016575 A1 * 1/2010 Yang et al. ....................... 536/56
2011/0059883 A1 * 3/2011 Swazey et al. ................ 510/320
2011/0104096 A1 * 5/2011 Swazey ...................... 424/70.13
2012/0309662 A1 * 12/2012 D'Ambrogio et al. ........ 510/218

FOREIGN PATENT DOCUMENTS

EP 0859011 A 8/1998
GB 2379223 A * 8/2001
JP 62172099 A 7/1987
JP 6043600 A 6/1994

(Continued)

OTHER PUBLICATIONS

PCT Search report for PCT/US07/83422 mailed Mar. 19, 2008.

PCT Search report for PCT/US07/87229 mailed Apr. 9, 2008.

Chinese Office Action Application No. 200780041617.6 Issued Dec. 21, 2010.

PCT Search Report for PCT/US07/87216, Date of mailing May 6, 2008.

Australian Examination Report of Singapore 200903483-6, mailed Jan. 25, 2011, Australian Patent Office, pp. 1-7.

(Continued)

*Primary Examiner* — Daniel S Metzmaier

(74) *Attorney, Agent, or Firm* — Sutherland Asbill & Brennan LLP

(57) ABSTRACT

Surfactant systems are provided using microfibrous cellulose to suspend particulates. In one embodiment the surfactant system includes a microfibrous cellulose at a concentration from about 0.05% to about 1.0% (w/w), a surfactant at a concentration of about 51% to about 99% (w/w active surfactant), and a suspended particulate. Also provided herein are methods for preparing surfactant systems including microfibrous cellulose.

21 Claims, No Drawings

(56) References Cited

FOREIGN PATENT DOCUMENTS

| | | | | |
|---|---|---|---|---|
| JP | 2000026229 | A | | 1/2000 |
| JP | 2003095904 | A | | 4/2003 |
| WO | 9940153 | A1 | | 8/1999 |
| WO | 0047628 | A2 | | 8/2000 |
| WO | WO 01/05838 | A1 | * | 1/2001 |
| WO | 0218486 | | | 3/2002 |
| WO | 03062361 | A1 | | 7/2003 |
| WO | 03085074 | A1 | | 10/2003 |
| WO | WO 2004/074420 | A1 | * | 9/2004 |
| WO | 2005048986 | A1 | | 6/2005 |
| WO | 2008057985 | A1 | | 5/2008 |

OTHER PUBLICATIONS

European Search Report/Opinion of EP07865575, mailed Dec. 1, 2011, EPO, The Hague, pp. 1-9.

Extended European Search Report/Opinion of EP07863824.4 , mailed Mar. 9, 2011, EPO, The Hague, pp. 1-13.

* cited by examiner

SURFACTANT THICKENED SYSTEMS COMPRISING MICROFIBROUS CELLULOSE AND METHODS OF MAKING SAME

CROSS-REFERENCE TO RELATED APPLICATIONS

The present application is a continuation-in-part of U.S. patent application Ser. No. 11/557,622 filed in the U.S. Patent and Trademark Office on Nov. 8, 2006. The disclosure of this application is incorporated herein by reference in its entirety.

BACKGROUND OF THE INVENTION

Surfactant-based products such as body washes, shampoos, bubble bath, dish soap, automatic dishwashing detergents, laundry detergents, automotive detergents, toilet cleaners, surfactant concentrates, fire-fighting foaming agents, among others, are often thickened by utilizing high concentration of surfactants, by combining viscosity synergistic surfactants, or by combining the surfactants with small amounts of salts, such as sodium salts. These formulations result in high viscosity products that appear rich and smooth but they are limited in that they do not provide sufficient low shear viscosity to allow for suspension of particles. Such particulates might include aesthetic agents (decorative beads, pearlescents, air bubbles, fragrance beads, etc.) or active ingredients (insoluble enzymes, encapsulated actives such as moisturizers, zeolites, exfoliating agents (e.g. alpha hydroxyl and/or glycolic acids or polyethylene beads), vitamins (e.g. vitamin E)) etc. or both.

Conventional thickeners and suspension aids such as xanthan gum, carboxymethyl cellulose (CMC), hydroxyethylcellulose (HEC), hydroxypropylmethylcellulose (HPMC), and many types of polyacrylates do not function well with high surfactant levels or in surfactant-thickened systems and often lead to a loss of transparency due to clouding, gelling, and/or phase separation or lack sufficient suspension properties. For example, xanthan gum imparts excellent suspension properties in certain body wash formulations with low surfactant-thickening but the gum often loses its suspension ability in systems with high surfactant thickening, usually resulting in a hazy, irregular appearance, and a grainy or lumpy texture. Cellulosic products (CMC, HEC, HPMC, etc.), as another example of conventional thickeners, provide unreliable suspension and have significant limitations with respect to surfactant compatibilities. Acrylates systems are common, however, these systems do not always achieve a sufficient clarity level, require high concentrations of polymer, and are not considered natural. Salts are often capable of increasing high shear viscosity in surfactant-thickened systems but do not impart long-term suspension ability.

There is presently a desire in the consumer products industry to provide for transparent surfactant-thickened systems with particulates suspended therein, as well as a suspension aid for high surfactant systems where many alternative thickeners will not function.

It has been discovered that microfibrous cellulose (MFC), bacterially derived or otherwise, can be used to provide suspension of particulates in surfactant-thickened systems as well as in formulations with high surfactant concentrations. It was also discovered that the MFC may be used for this purpose with or without co-agents. When bacterially-derived microfibrous cellulose is utilized, cellular debris can be eliminated which results in transparent solutions at typical use levels.

The microfibrous cellulose appears unaffected by the surfactant micelle development and maintains good suspension in these systems. Microfibrous cellulose is unique in its ability to function in these systems in large part because it is dispersed rather than solubilized, thereby achieving the desired suspension properties in formulations that would otherwise display the hazing and/or precipitation often seen using alternative solubilized polymers.

BRIEF SUMMARY OF THE INVENTION

Surfactant systems comprising microfibrous cellulose are described. "Surfactant systems" is intended to include but is not limited to surfactant-thickened and high surfactant systems. Microfibrous cellulose (MFC) includes MFC prepared by microbial fermentation or MFC prepared by mechanically disrupting/altering cereal, wood, or cotton-based cellulose fibers. When bacterially-derived microfibrous cellulose is utilized, cellular debris can be eliminated which results in transparent solutions at typical use levels. The present invention utilizes surfactants to achieve a very thick (highly viscous) system at high shear rates with particulates suspended therein by using microfibrous cellulose.

The surfactant concentration of these systems ranges from about 5% to about 99% (w/w active surfactant) wherein the specific concentration is product dependent. Body washes typically contain about 5% to about 15% (w/w) surfactant, dishwashing liquids typically contain about 20% to about 40% (w/w) surfactant (with 40% being an "ultra" concentrated product), and laundry detergents typically contain about 15% to about 50% (w/w) surfactant. Industrial surfactant concentrates (for later dilution by manufacturing or the consumer) can have surfactant levels near 100% for non-ionic surfactants, and sometimes over 50% for anionic surfactants. These concentrates can be used in the manufacture of consumer products such as bath soaps and shampoos or for applications such as fire-fighting foams where the surfactant is diluted in use. The MFC can be added to these concentrates to provide yield stress to the concentrate or to the diluted system. The MFC is present at concentrations from about 0.05% to about 1.0%, but the concentration will depend on the desired product. For example, while about 0.06% (w/w) MFC is preferred for suspending small air bubbles in an 80% surfactant system, about 0.078% is preferred for suspending air bubbles in a 99% surfactant system, and about 0.150% (w/w) is preferred for suspending either air bubbles or beads in a system containing about 40% (w/w) surfactant. Furthermore, the concentration of MFC will be adjusted accordingly if a highly transparent system is desired. Specifically, a very transparent body wash at about 5% to about 15% (w/w active surfactant) can be achieved with a MFC level of from about 0.055 to about 0.25% (w/w active surfactant).

Particulates to be suspended could include aesthetic agents (decorative beads, pearlescents, air bubbles, fragrance beads, etc.) or active ingredients (insoluble enzymes, encapsulated actives such as moisturizers, zeolites, exfoliating agents (e.g. alpha hydroxyl and/or glycolic acids or polyethylene beads), vitamins (e.g. vitamin E) etc. or both. Other suitable particulates would be apparent to one of skill in the art.

The invention is also directed to the use of co-agents and/or co-processing agents such as CMC, xanthan, and/or guar gum with the microfibrous cellulose in the surfactant systems described herein. Microfibrous cellulose blends are microfibrous cellulose products which contain co-agents. Two blends are described MFC, xanthan gum, and CMC in a ratio of 6:3:1, and MFC, guar gum, and CMC in a ratio of 3:1:1. These blends allow MFC to be prepared as a dry product which can be "activated" with high shear or high extensional mixing into water or other water-based solutions. "Activation" occurs when the MFC blends are added to water and the co-agents/co-processing agents are hydrated. After the hydration of the co-agents/co-processing agents, high shear is generally then needed to effectively disperse the microfibrous cellulose fibers to produce a three-dimensional functional network that exhibits a true yield point. Unexpectedly, the co-agent and/or co-processing agents CMC, xanthan, and/or guar gum present in these microfibrous cellulose blends appear to remain solubilized (after activation in water) in many high surfactant formulations despite their general lack of compatibility in the high surfactant systems, most likely due to the low use level of these polymers in these formulations with MFC.

The invention is further directed to methods of making the surfactant systems described, with or without co-agents and/or co-processing agents.

BRIEF DESCRIPTION OF THE SEVERAL VIEWS OF THE DRAWINGS

The foregoing summary will be better understood when read in conjunction with the Detailed Description of the Invention.

DETAILED DESCRIPTION OF THE INVENTION

Solutions containing high levels of surfactant were prepared using microfibrous cellulose with and without co-agents. The pH of the systems described herein range from about 2 to about 12.

Example 1

A thickened solution containing 80% non-ionic surfactant was prepared with 0.1% microfibrous cellulose blend (MFC/xanthan/CMC 6:3:1 blend). A concentrate was first prepared containing 0.5% microfibrous cellulose blend (MFC/xanthan/CMC 6:3:1 blend) in deionized water. 40 g of this solution was introduced into a 250 ml beaker and then 160 g of undiluted Triton® X-100 (~100% active Octoxynol-9 from Union Carbide) was added slowly with mixing at 600 rpm using a jiffy mixing blade. The resulting solution exhibited good clarity upon visual inspection and possessed the ability to suspend polyethylene beads, gelatin encapsulates, gellan gum beads, and air bubbles. The yield value was 0.33 Pa (as measured with a Brookfield® Yield Rheometer) at a pH of 5.3.

Example 2

A thickened solution containing 80% non-ionic surfactant was prepared with 0.1% microfibrous cellulose blend (MFC/xanthan/CMC 6:3:1 blend). A concentrate was first prepared containing 0.5% microfibrous cellulose blend (MFC/xanthan/CMC 6:3:1 blend) in deionized water. 40 g of this solution was put into a 250 ml beaker and 160 g of undiluted Tween® 20 (~100% active Polysorbate 20 from ICI) was added slowly with mixing at 600 rpm using a jiffy mixing blade. The resulting solution exhibited good clarity upon visual inspection and possessed the ability to suspend polyethylene beads, gelatin encapsulates, gum arabic encapsulates, and air bubbles. The yield value was 0.11 Pa (as measured with a Brookfield® Yield Rheometer) at a pH of 6.0.

Example 3

A thickened solution containing 99% non-ionic surfactant was prepared using a wet-cake version of microfibrous cellulose. 0.78% wet cake was added to undiluted Triton X-100 and mixed on an Oster® blender at "liquefy" (top speed) for 5 minutes. The activity (% solids) of this wet-cake form of MFC was about 16% so the active MFC level was 0.125% in the surfactant. The resulting solution exhibited good clarity upon visual inspection and possessed the ability to suspend polyethylene beads, gelatin encapsulates, gum arabic encapsulates, and air bubbles. The solution was de-aerated under vacuum and the yield point was taken. Upon visual inspection the resulting solution exhibited good clarity with a slight haze and a yield point of 14.6 Pa.

Example 4

A thickened solution containing 99% non-ionic surfactant was prepared using the wet-cake version of microfibrous cellulose. 0.78% wet cake was added to undiluted Tween® 20 and mixed on an Oster® blender at "liquefy" (top speed) for 5 minutes. The activity (% solids) of this wet-cake form of MFC was 16% resulting in an active MFC level of 0.125% in the surfactant. The resulting solution exhibited good clarity upon visual inspection and possessed the ability to suspend polyethylene beads, gelatin encapsulates, gum arabic encapsulates, and air bubbles. The solution was de-aerated under vacuum and the yield point was determined. Upon visual inspection the resulting solution exhibited good clarity with some haze and a yield point of 17.8 Pa.

The invention claimed is:

1. An aqueous composition comprising a high surfactant system consisting essentially of water, a microfibrous cellulose present in the aqueous composition at a concentration from about 0.05% to about 0.155% (w/w), a surfactant present in the aqueous composition at a concentration from about 51% to about 99% (w/w active surfactant), and a suspended particulate, wherein the aqueous composition is clear.

2. The aqueous composition according to claim 1, wherein the microfibrous cellulose is present in the aqueous composition at a concentration from about 0.06% to about 0.125%.

3. The aqueous composition according to claim 2, wherein the surfactant is present in the aqueous composition at a concentration from about 80% (w/w active surfactant) to about 99%.

4. The aqueous composition according to claim 3, wherein the suspended particulate comprises air bubbles.

5. The aqueous composition of claim 3, wherein the pH is from about 3 to about 11.

6. The aqueous composition according to claim 1, wherein the microfibrous cellulose is present in the aqueous composition at a concentration from about 0.075% to about 0.125%.

7. The aqueous composition according to claim 1, wherein the microfibrous cellulose is present in the aqueous composition at a concentration of about 0.125%.

8. The aqueous composition of claim 1, wherein the surfactant comprises a non-ionic surfactant, an anionic surfactant, or a combination thereof.

9. The aqueous composition of claim 1, wherein the microfibrous cellulose comprises a blend of a microfibrous cellulose, xanthan gum, and carboxymethylcellulose in a ratio of 6:3:1.

10. The aqueous composition of claim 1, wherein the microfibrous cellulose comprises a blend of a microfibrous cellulose, guar gum, and carboxymethylcellulose in a ratio of 3:1:1.

11. A surfactant system comprising a microfibrous cellulose, a surfactant, and a suspended particulate, wherein the microfibrous cellulose is present at a concentration of about 0.125% and the surfactant is present at a concentration of about 99% (w/w active surfactant).

12. The surfactant system of claim 11, wherein the pH is from about 3 to about 11.

13. Method of preparing a surfactant system comprising:

combining a microfibrous cellulose with water and mixing with high shear, adding a surfactant and then mixing, and adding particulates followed by mixing, wherein the microfibrous cellulose is present at a concentration from about 0.05% to about 0.15% (w/w), the surfactant is present at a concentration from about 51% to about 99% (w/w active surfactant), and the resulting system is clear and the particulates are suspended therein.

14. The method of claim 13 wherein the microfibrous cellulose is present at a concentration from about 0.06% to about 0.125%.

15. The method of claim 13, wherein the microfibrous cellulose is present at a concentration from about 0.075% to about 0.125%.

16. The method of claim 13, wherein the microfibrous cellulose is present at a concentration of about 0.125%.

17. The method of claim 13, wherein the surfactant is present at a concentration from about 80% (w/w active surfactant) to about 99%.

18. The method of claim 13, wherein the surfactant comprises a non-ionic surfactant, an anionic surfactant, or a combination thereof.

19. The method of claim 13, wherein the microfibrous cellulose comprises a blend of a microfibrous cellulose, xanthan gum, and carboxymethylcellulose in a ratio of 6:3:1.

20. The method of claim 13, wherein the microfibrous cellulose comprises a blend of a microfibrous cellulose, guar gum, and carboxymethylcellulose in a ratio of 3:1:1.

21. Method of preparing a surfactant system comprising a microfibrous cellulose, a surfactant, and particulates comprising:

combining a microfibrous cellulose with water and mixing, adding a surfactant and then mixing, and adding particulates followed by mixing, wherein the microfibrous cellulose is present at a concentration of about 0.05% to about 1.0% (w/w) and the surfactant is present at a concentration of about 99% (w/w active surfactant); and wherein the resulting system is clear and the particulates are suspended therein.

* * * * *